United States Patent [19]

Johanson et al.

[11] 4,446,717
[45] May 8, 1984

[54] ABRASIVE WEAR TESTER

[75] Inventors: Jerry R. Johanson, Chelmsford; Thomas A. Royal, Arlington, both of Mass.

[73] Assignee: Jenike & Johanson, Inc., No. Billerica, Mass.

[21] Appl. No.: 402,632

[22] Filed: Jul. 28, 1982

[51] Int. Cl.³ .............................................. G01N 3/56
[52] U.S. Cl. ........................................................ 73/7
[58] Field of Search .......................................... 73/7, 86

[56] References Cited

U.S. PATENT DOCUMENTS

| | | | |
|---|---|---|---|
| 1,476,775 | 12/1923 | Sproull | 73/7 |
| 1,961,333 | 6/1934 | Burns | 73/51 |
| 3,653,252 | 4/1972 | Neff et al. | 73/7 |

FOREIGN PATENT DOCUMENTS

| | | | |
|---|---|---|---|
| 200267 | 9/1967 | U.S.S.R. | |
| 269544 | 8/1970 | U.S.S.R. | |
| 321718 | 1/1972 | U.S.S.R. | |
| 386317 | 9/1973 | U.S.S.R. | |
| 502293 | 4/1976 | U.S.S.R. | |
| 673884 | 7/1979 | U.S.S.R. | 73/7 |

Primary Examiner—S. Clement Swisher
Attorney, Agent, or Firm—Kenway & Jenney

[57] ABSTRACT

Apparatus for testing abrasive wear on a surface of a sample. Flowable abrasive material is fed from a barrel against the surface. The sample is mounted reciprocally in the direction of feeding of the material, and urged by a force opposing that of the material thereon. The rate of feeding is controlled to maintain a gap between the end of the barrel and the sample so that the material flows continuously through the gap.

22 Claims, 4 Drawing Figures

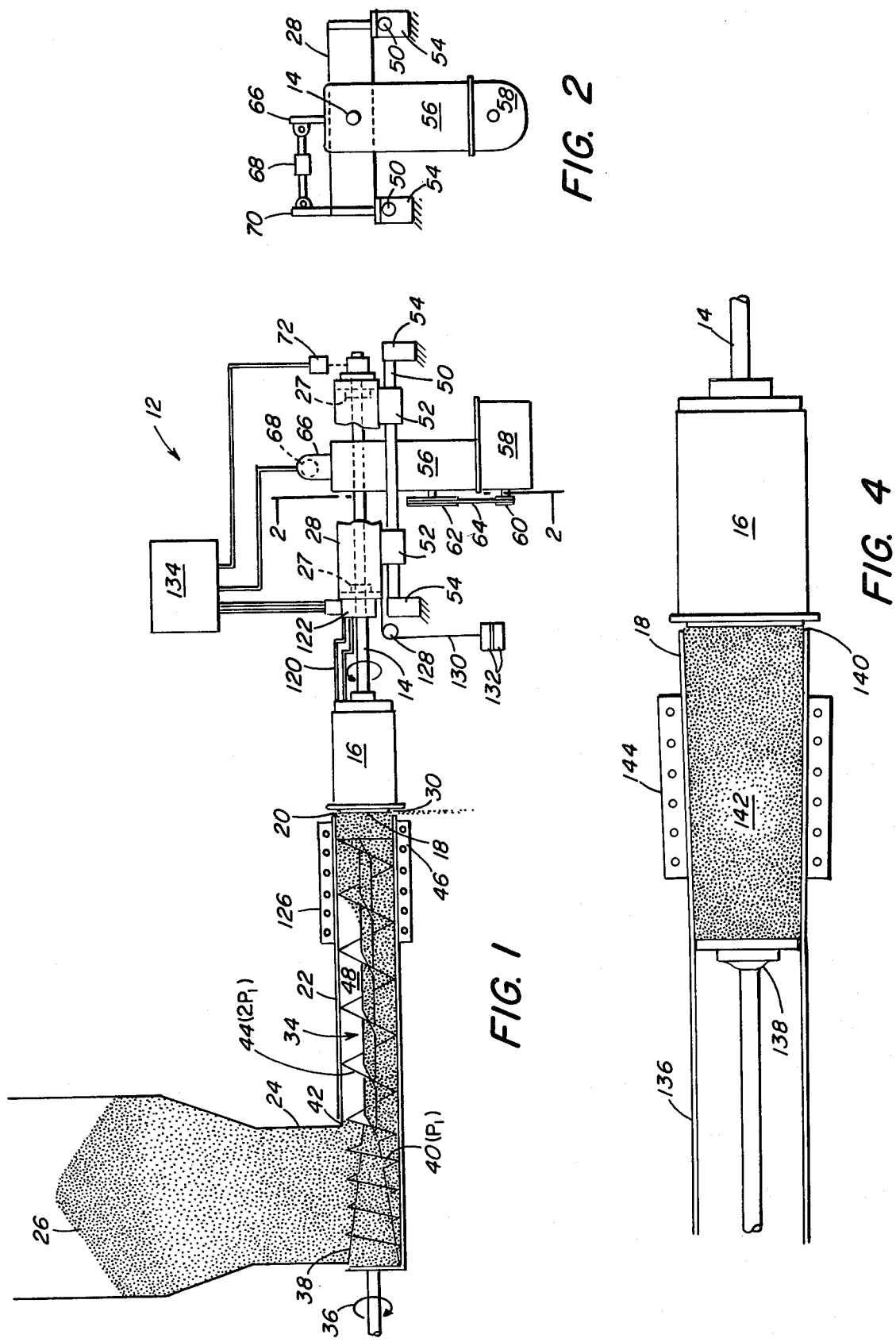

ABRASIVE WEAR TESTER

SUMMARY OF THE INVENTION

This invention relates generally to apparatus for testing the wear of an abrasive material upon a surface of a test sample. More particularly, it relates to a wear tester in which a flowable abrasive material impinges on the surface under conditions that are not materially influenced by any adjacent wearing surface.

Abrasive wear is a common problem in equipment of a wide variety. Common causes of abrasion are particulate solids, and the abrasive effect of these solids is a function of their physical properties and of the configuration and operation of the equipment in service. Problems to which the present invention is directed are exemplified by the storing and handling of abrasive bulk granular or particulate solids in bins, hoppers, feeders, conveyors, chutes and the like. In designing such equipment, it is desirable to predict the wear rate of a given wear material subjected to the sliding of a given bulk granular solid thereon in operation. This prediction will be reflected in the design of the equipment, so that the wearing surfaces will be hard and thick enough, and if necessary replaceable, so that required maintenance can be minimized or avoided for the expected service life of the equipment.

In practice, the design engineer can predict the wear rate by a two-step process. The first step is to predict the velocity and pressure of the bulk solids at the wear surface, and the second step is to determine the wear rate as a function of the bulk solids pressure at the surface. The first step is both empirical and theoretical in nature, and establishes the bulk solids velocity and pressure at the wear surface by application of solids flow theory to the equipment geometry, taking into account the experimentally measured flow properties of the given bulk solid. The second step is performed with the aid of a body of test data obtained empirically, and establishes the wear rate as a function of the bulk solids pressure at the surface of the given wear material. This test data is obtained by measurement of wear on a sample in a suitable wear testing apparatus. Since the solids pressure and velocity distribution can be computed in the first step, and since wear rate can be experimentally established in the second step as a function of various solids pressures, the wear rate at any location in the equipment under design can be predicted.

It is evident that suitable wear testing apparatus for performing the second step should simulate as closely as possible the conditions of wear experienced by the equipment under design. In a tester simulating the conditions that exist in equipment for storing and handling abrasive bulk granular solids, the most important requirements are:

(1) A fresh supply of bulk solid must be presented continually to the wearing surface. The ever new bulk solid particles at the wear surface, being irregular in shape, cause stress concentrations above the elastic limit of the wearing surface material at points of contact. This is the mechanism of wear generally referred to as abrasion. Failure to refresh the abrasive bulk solid at the wear surface in a test apparatus leads to erroneous results because the particles themselves can wear and become rounded, thereby reducing stress concentrations in the wear surface material and hence, reducing the consequential abrasive wear.

(2) The solids pressure exerted on the wear sample surface must be continuously controlled and measured, as the wear results are recorded against this pressure. In this connection, it is obvious that the pressure distribution at the wear surface in the test apparatus should be as uniform as possible.

(3) The relative velocity between the bulk solid and the wear material must be controlled and measured.

(4) The shear stress exerted on the wear material should be continuously measured so that any changes in the coefficient of friction between the bulk solid and the wear surface can be observed as the latter is worn.

A wide variety of wear testing apparatus has been employed in the prior art. Many such testers employ so-called "two-body abrasive wear," that is, wear that occurs between a wearing surface and a fixed matrix of abrasive particles. An example of such a fixed matrix is sandpaper. This type of apparatus would be suitable for simulating such conditions as arise in material removal processes such as sanding and grinding. It is generally recognized that testing apparatus of this type does not provide useful data with reference to the storing and handling of abrasive bulk granular solids because the latter are free to roll along the wearing surface and the magnitude of wear may be an order of magnitude less than in the case of "two-body abrasive wear."

There has been relatively little research on so-called "three-body abrasive wear," defined as wear due to loose abrasive particles sliding on a wearing surface. A treatment of this type of wear is given by Misra, A. and Finnie, I., "A Classification of Three-Body Abrasive Wear and Design of a New Tester," *Wear*, 60 (1980) pp. 111-121. The authors classify three-body abrasive wear as "closed" or "open." Closed three-body abrasive wear pertains to wear due to loose abrasive particles being trapped between two closely spaced rolling or sliding wear surfaces. Test apparatus designed for producing this type of wear would be of value, for example, in predicting the premature failure of bearings caused by contaminate particles of dirt. Open three-body abrasive wear pertains to wear occuring when the wearing surfaces are far apart, or when only one wearing surface exists. Wear from the flow of bulk solids falls into the open classification.

Accordingly, it is a principal object of this invention to provide improved wear testing apparatus in which open three-body abrasive wear on a test surface occurs.

A second object of the invention is to provide a wear tester of this classification in which means are provided to vary the gap between the wear sample and the means of delivering the abrasive bulk granular solids to its surface, as desired.

A third object is to provide apparatus in which the flow rate of the abrasive particles can be controlled without affecting the pressure distribution applied to the wearing sample.

A fourth object is to produce a uniform stress distribution acting on the wearing surface, particularly when the bulk solids are fed from a barrel or the like, with means to isolate the sample from the stress concentrations caused by particles being caught in the gap at the end of the barrel.

A fifth object is to provide a tester in which the applied load is independent of the quantity of abrasive solids in the test apparatus at any given time.

With the foregoing and other objects hereinafter appearing in view, the features of this invention include the provision of apparatus for applying open three-body abrasive wear to a sample which is supported rotatably about and reciprocally along an axis. A barrel is provided for containing a flowable abrasive material extending along the axis and having an open end facing a surface of the sample. Means are provided to feed the material in the barrel toward said surface at a controlled rate. Means are further provided for urging the sample toward the barrel with a force opposed to that of the material on the sample. The rate of feeding the material toward said surface is controlled to maintain a gap between the sample and said open end, whereby the abrasive material flows continuously through the gap.

The means for feeding the material in the barrel may comprise a plunger, in which case the cross sectional area of the barrel preferably increases in the direction toward the open end. The means for feeding may also comprise a screw feeder. When such a feeder is employed, the pitch of the screw may vary along its length so that a portion of the barrel between the hopper or other source of the material and the open end will be only partially filled with the abrasive material, thereby isolating the hopper from the pressure conditions at the open end.

Another feature comprises means for allowing the sample to move away from the open end of the barrel upon a sudden increase in the force of the material due to the passage of a solid particle or lump of relatively large dimension through the gap.

The surface of the test specimen subjected to wear is preferably located inwardly of the opening in the end of the barrel, thus isolating the wear surface from the high stress concentrations that occur at the periphery of such opening.

The test apparatus includes means for rotating the sample and measuring the number of revolutions thereof in a test cycle. Means are also provided for measuring the torque on the sample, the force of the bulk solids on the sample, and its temperature.

Other features of the invention comprise the structures for achieving these and other features as hereinafter more fully described and shown in the drawings.

DRAWING

FIG. 1 is a partially schematic drawing illustrating a presently preferred embodiment of the invention employing a screw feeder.

FIG. 2 is an axial view taken on line 2—2 of FIG. 1.

FIG. 4 is an illustration of an alternative plunger feeder for the bulk solids.

DETAILED DESCRIPTION

Figure 3:
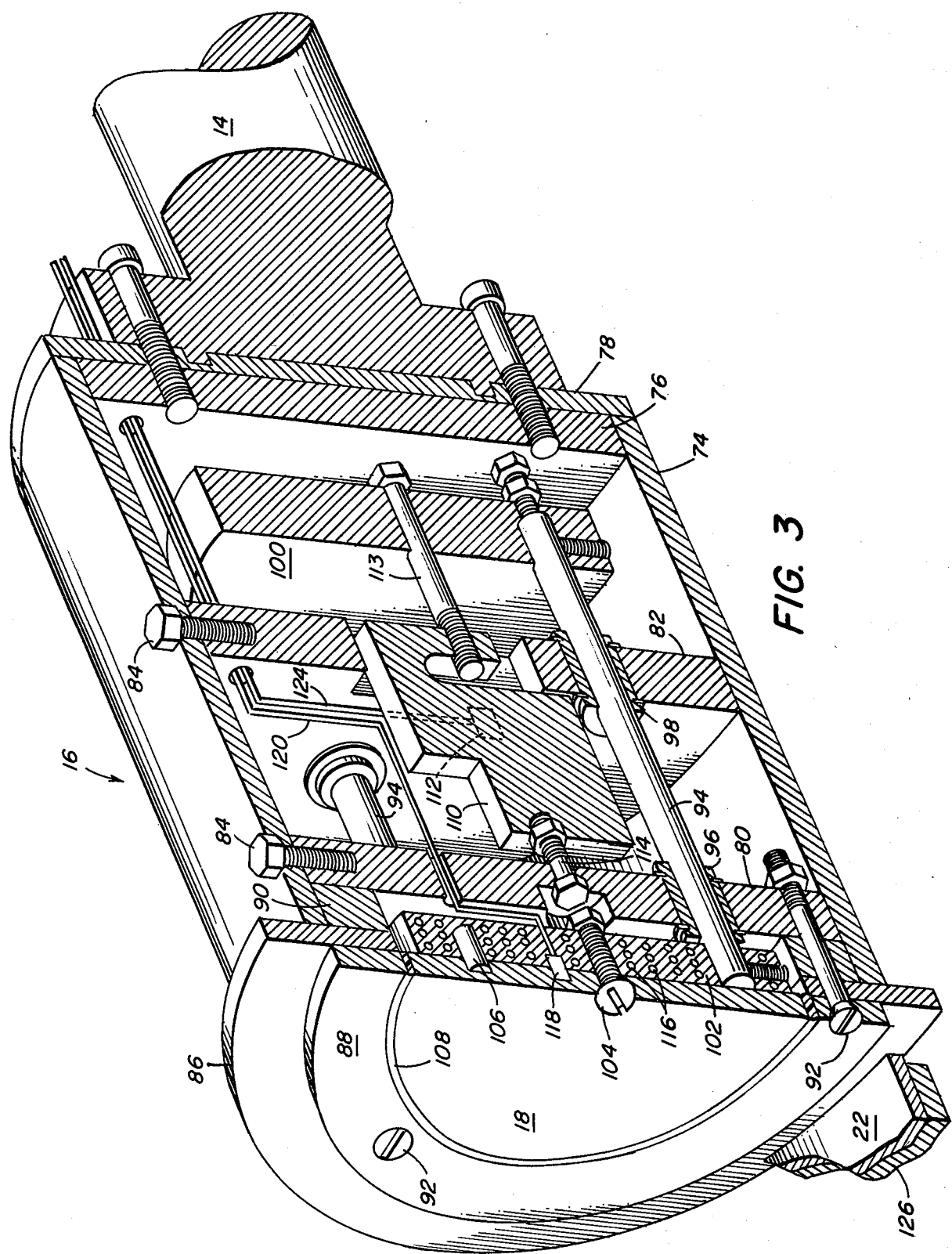
FIG. 3 is a diagonal elevation in section illustrating the sample holding module.

FIG. 1 illustrates a presently preferred form of abrasive wear testing apparatus according to this invention, designated generally by the reference number 12. The apparatus includes a rotating shaft 14 to which is attached a sample holding module 16, the sample being of circular disk shape and shown at 18. Details of the sample disk and the supporting module are shown in FIG. 3.

Facing the disk 18 is the open end 20 of a screw barrel 22 having one end connected with a hopper 24 containing a quantity of abrasive bulk particulate or granular solids 26.

The shaft 14 is supported rotatably in suitable bearings 27 in a frame 28 that is reciprocal in the axial direction of the shaft. The frame 28 is urged by a predetermined force in the direction toward the barrel 22. In operation, this force is opposed by the equal force of the bulk solid 26 impinging on the facing end of the sample holding module 16. This balance of forces obtains while the module 16 is rotating with a gap 30 existing between the open end 20 of the barrel and the sample holding module, and with bulk solid material flowing continuously from the apparatus through this gap.

Referring more particularly to the hopper and feeder portion of the test apparatus, the hopper 24 is preferably a mass flow hopper, that is, a hopper so designed according to presently available technology in the industry that all of the material within it is in motion while any material is being withdrawn from it. The hopper discharges into the cylindrical screw barrel 22 fitted with a feed screw 34. A suitable drive (not shown) is provided for rotating the screw 34 independently of a motor 58 which drives the shaft 14 and in the direction indicated by an arrow 36. The angular direction of the arrow 36 is opposite to that of the shaft 14. At the outlet of the hopper the screw is provided with a shaft section 38 of tapered configuration, over which there is a blade section 40 coextensive with the outlet of the hopper and having a pitch $P_1$. Between the sections 38 and 40 and the end 20 of the barrel, there is a blade section 44 having a pitch $2P_1$. The section 44 ends at a point 46 spaced a predetermined distance from the end 20 in order to smooth out fluctuations in the solids contact pressure on the module 16 due to the end of the screw flights. The purpose of the section 44 of increased pitch is to provide a reduction in the feed efficiency, that is, a condition in which a portion of the length of the barrel is only partially filled with solids and within which there is an open space 48. In operation, the space 48 may vary in volume under certain conditions, depending upon the force being developed between the bulk solids and the module. The presence of the space 48 is important in cases where bulk solids that flow with difficulty are employed and where the back pressure from the wear sample might otherwise cause flow problems in the hopper. Also, since the section 44 is less than 100% filled, less torque is required to turn the screw 34.

Referring more particularly to the apparatus for supporting and rotating the sample 18, the frame 28 is supported on two parallel horizontal shafts 50 by two pairs of linear ball bearings 52. The shafts 50 are fixed by supports 54.

A geared speed reducer 56 is mounted on and drives the shaft 14. The variable speed motor 58 is secured to the speed reducer 56 and has connection therewith via pulleys 60 and 62 and a belt 64.

A torque arm 66 (FIG. 2) is affixed to the speed reducer 56 and is attached to one side of a load cell 68 fitted with a strain gage adapted for producing an electrical signal indicative of the force exerted thereon by the torque arm. The other side of the load cell is connected to a support 70 fixed to the frame 28. In operation, the force indicated by the load cell 68 is proportional to the torque applied to the shaft 14 by the internal speed reduction gearing of the speed reducer 56 (not shown), which torque is in turn equal to the torque applied to the end of the module 16 by the bulk solids 26, except for the relatively small and negligible friction in the shaft bearings 27.

A revolution counter 72 of conventional construction is operably associated with the shaft 14 and provides a signal indicative of the number of shaft rotations during a test cycle.

Details of the sample holding module 16 are shown in FIG. 3. The module has a frame comprising a cylindrical body 74 having back end plates 76 and 78 suitably secured to it, and partition plates 80 and 82 secured within it by screws 84. The plate 78 is secured to the shaft 14. The frame further includes a front end plate 86, a hardened replaceable faceplate ring 88 and a spacer ring 90 secured by screws 92 to the partition plate 80.

The frame thus described comprises a rigid assembly within which a sample subassembly having three equally spaced shafts 94 is reciprocal in linear ball bearings 96 and 98 mounted in the partition plates 80 and 82, respectively. The shafts 94 are fastened by set screws or similar means to a disk 100 which is situated in spaced relationship to the body 74, the backplate 76 and the partition plate 82. At their respective front ends, the shafts 94 are secured by set screws or similar means to a sample support disk 102 that is situated in spaced relationship to the partition plate 80. The sample disk 18 is secured to the sample support by a screw 104, and is rotatably fixed in relation to the support 102 by one or more suitable torque pins 106. A gap 108 separates the sample 18 from the faceplate ring 88, and in use, this gap is filled with a flexible abrasion resistant silicone sealant to prevent solid particles from wedging into the gap, while being flexible enough to allow axial movement between sample 18 and the faceplate ring 88.

A load cell 110 having a suitable strain gage 112 and being of conventional construction is mounted in spaced relationship to the partition plates 80 and 82. One end of the load cell is connected to the disk 100 by a screw 113 and the other end is connected to the partition plate 80 by a screw 114. Thus, it will be seen that pressure on the sample 18 is transmitted through the shafts 94 to the disk 100, thereby developing an equal tension force in the screw 112. This force is opposed by an equal and opposite tension force on the screw 114, urging the frame of the load cell in the direction of the force applied to the sample.

The open end 20 of the barrel 22 is preferably opposed to the outer periphery of the faceplate ring 88, whereby the entire area of the sample 18 is located inwardly in radially spaced relation to the end 20. This arrangement is preferred in order to make the pressure distribution on the sample 18 as uniform as possible. It has been found that in operation, stress concentrations occur as lumps of bulk solids are squeezed through the gap 30 between the faceplate ring 88 and the barrel, and with this construction these stresses apply a force directly to the frame of the module 16. Thus the load cell 110 is isolated from such forces.

The illustrated construction facilitates the replacement of the faceplate ring 88 whenever, after a number of tests, the abrasive wear has significantly worn its surface. It also facilitates the rapid mounting and dismounting of the sample 18. The sample is merely fitted within the faceplate ring 88 against the mounting plate 102 with the torque pins in place, and held in position by the screw 104. The silicone or other equivalent sealant is then applied to the gap 108. After the test is completed, the screw 104 is removed and the sealant is ruptured to permit dismounting of the specimen.

Specimens of different thicknesses can be tested by providing a number of mounting plates 102 of differing thicknesses in combination with adjustment of the screw 113. Thus the exposed face of the sample will be located in the same plane relative to the faceplate ring.

In cases where it is desired to test the wear of the sample at a predetermined temperature, the mounting plate 102 can incorporate suitable heating elements illustrated by resistance wires 116 connected to a suitable source of current through slip rings (not illustrated), and suitable insulation can be provided to isolate the load cell 110 from this source.

A thermocouple 118 is located on the mounting plate 102 in intimate contact with the sample 18, and connected by wiring 120 to slip rings illustrated at 122. Similarly, the load cell 110 is connected by wiring 124 to the slip rings.

In certain tests where the bulk solids are to be tested at predetermined elevated temperatures, it is desirable to provide heating means 126 around the barrel 22.

The force of the bulk solids on the module 16 is opposed by an equal horizontal force applied to the frame 28 by means of a pulley 128, a pulley wire 130 and weights 132.

A recorder 134 of any suitable type is provided for recording the test results as a function of time, such results including correlated readings of the sample temperature, the pressure force on the sample 18 itself, the torque applied to the module by the bulk solids and the number of revolutions during the test cycle.

A typical test cycle is begun by selecting a desired combination of applied weights 132 producing a predetermined axial force on the shaft 14. The drive means for the screw 34 are energized to start the feeding of bulk solids against the opposed face of the module 16. The motor 58 is energized to begin rotation of the module, and a gap 30 is thereby produced, with the solids flowing continuously therethrough. The speed of the motor 58 is controlled to avoid an excessive temperature of the sample 18. Although the force of the solids applied to the end of the module during a test run will be constant and equal to the force determined by the applied weights 132, the feed rate of the solids and the size of the gap 30 may be varied. Thus if the feed rate is increased, the gap 30 will correspondingly increase to maintain the same force on the module, and if the feed rate is decreased, the gap 30 will decrease with the same results. Wear on the sample is measured as the weight loss for a certain number of revolutions of the sample 18.

FIG. 4 shows an alternative feeder for the bulk solids. This comprises a flared barrel 136 containing a plunger 138 driven by suitable screw means (not shown). The barrel is tapered so that its cross sectional area increases toward the open end 140. This taper provides the advantage that it allows movement of the abrasive material 142 without excessive plunger force. If desired, this embodiment may also be provided with heating means 144 such as a resistance heating element or the like.

We claim:

1. Apparatus for applying abrasive wear to a surface of a sample including, in combination, support means for mounting the sample rotatably about and reciprocally along an axis, a barrel for containing a flowable abrasive material extending along the axis and having an open end facing said surface, means to feed the material in the barrel toward said surface at a controlled rate, and means for urging the sample toward the barrel with a force opposed to that of the material on the sample, said controlled rate being sufficient to maintain a gap between the sample and said open end, whereby the material flows continuously through the gap.

2. The combination of claim 1, in which the means to feed the material comprise a plunger.

3. The combination of claim 2, in which the cross sectional area of the barrel increases in the direction toward said open end.

4. The combination of claim 1, in which the means to feed the material comprise a screw feeder.

5. The combination of claim 4, with a hopper to supply the material to the barrel at a position along the length thereof, the screw feeder having a pitch that varies along its length to cause the material to fill the barrel partially within a section along said length between said position and said open end.

6. The combination of claim 5, in which the hopper has a discharge opening and the screw feeder has a shaft with a diameter tapering downwardly toward said open end.

7. The combination of claim 1, in which the means to feed are adapted for feeding bulk particulate abrasive solids.

8. The combination of claim 7, in which said means for urging the sample are adapted to allow it to move away from said open end upon a sudden increase in the force of the material thereupon due to the passage of a solid particle of relatively large dimension through the gap.

9. The combination of claim 1, in which said surface is smaller in area than said open end and located in spaced relation to its periphery.

10. The combination of claim 1, with means for measuring said force.

11. The combination of claim 10, with means for measuring the torque applied to the sample.

12. The combination of claim 10, with means for counting the revolutions of the sample.

13. The combination of claim 1, with means for applying heat to the material through the barrel.

14. The combination of claim 1, with means for applying heat to the sample.

15. The combination of claim 1 or claim 9, in which the support means comprise
   a rotatable body,
   an annular faceplate ring on one end of the body,
   sample mounting means supported by the body reciprocally therein in the direction of said axis and adapted to mount the sample within the faceplate ring,
   and loadcell means adapted to communicate forces between the sample mounting means and body and adapted to produce a signal varying with said last mentioned forces and resulting from the force of the material on the sample.

16. The combination of claim 15, in which the sample mounting means are adapted to mount the sample in radially spaced relation to the faceplate ring, whereby the loadcell is isolated from the force of the material on the faceplate ring.

17. The combination of claim 1, in which said axis is substantially horizontal.

18. The combination of claim 1, in which the material is fed through the barrel at a constant rate.

19. The combination of claim 1, in which said force is maintained constant.

20. The combination of claim 1, in which said axis is substantially vertical.

21. The combination of claim 1, with means for rotating the support means at a predetermined speed.

22. The combination of claim 21, in which the speed of rotation of the support means is controlled independently of said controlled rate of feeding the material.

* * * * *